United States Patent [19]

Gutman

[11] 4,251,263
[45] Feb. 17, 1981

[54] N-SUBSTITUTED, 2-PHENOXYNICOTINAMIDE COMPOUNDS AND THE HERBICIDAL USE THEREOF

[75] Inventor: Arnold D. Gutman, Berkeley, Calif.

[73] Assignee: Stauffer Chemical Company, Westport, Conn.

[21] Appl. No.: 72,387

[22] Filed: Sep. 4, 1979

[51] Int. Cl.$^3$ .................... A01N 43/40; C07D 213/56
[52] U.S. Cl. ........................................ 71/94; 546/291
[58] Field of Search ........................... 546/291; 71/94

[56] References Cited

U.S. PATENT DOCUMENTS

| | | | |
|---|---|---|---|
| 3,228,950 | 1/1966 | Renk et al. | 546/291 |
| 3,398,155 | 8/1968 | Horrom | 546/323 |
| 3,822,278 | 7/1974 | Dufour | 546/291 |
| 4,061,642 | 12/1977 | Fleckenstein et al. | 546/291 |
| 4,146,637 | 3/1979 | Metz et al. | 546/291 |

FOREIGN PATENT DOCUMENTS 7705037  11/1977  Netherlands ................. 71/94

OTHER PUBLICATIONS

Chem. Soc. Journ. London (Kruger et al.) 1954, p. 3905.
Chem. Soc. Journ. London (Kruger et al.) 1955, p. 2755.
Fujikawa et al., Agr. Biol. Chem., vol. 34, No. 1, pp. 68–79, (1970).

*Primary Examiner*—Ethel G. Love
*Attorney, Agent, or Firm*—Joel G. Ackerman

[57] ABSTRACT

This invention relates to novel herbicidal compounds having the formula

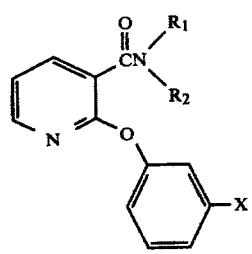

in which X is chloro, bromo, trifluoromethyl, methyl or ethyl; $R_1$ is hydrogen or $C_3$–$C_5$ alkenyl; and $R_2$ is (a) $C_3$–$C_5$ alkenyl if $R_1$ is $C_3$–$C_5$ alkenyl; (b) $C_3$–$C_5$ alkyl, $C_3$–$C_5$ alkenyl or $C_3$–$C_6$ alkynyl if X is chloro, methyl, ethyl or trifluoromethyl and $R_1$ is hydrogen; and (c) $C_1$–$C_5$ alkyl, $C_3$–$C_5$ alkenyl or $C_3$–$C_6$ alkynyl if X is bromo and $R_1$ is hydrogen.

These compounds have been found to exhibit herbicidal properties.

24 Claims, No Drawings

N-SUBSTITUTED, 2-PHENOXYNICOTINAMIDE COMPOUNDS AND THE HERBICIDAL USE THEREOF

BACKGROUND OF THE INVENTION

This invention relates to novel herbicidal compounds having the formula

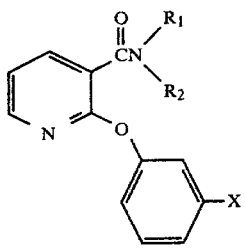

in which X is chloro, bromo, trifluoromethyl, methyl or ethyl; $R_1$ is hydrogen or $C_3$-$C_5$ alkenyl; and $R_2$ is (a) $C_3$-$C_5$ alkenyl if $R_1$ is $C_3$-$C_5$ alkenyl; (b) $C_3$-$C_5$ alkyl, $C_3$-$C_5$ alkenyl or $C_3$-$C_6$ alkynyl if X is chloro, methyl, ethyl or trifluoromethyl and $R_1$ is hydrogen; and (c) $C_1$-$C_5$ alkyl, $C_3$-$C_5$ alkenyl or $C_3$-$C_6$ alkynyl if X is bromo and $R_1$ is hydrogen.

These compounds have been found to exhibit herbicidal properties.

The term "$C_3$-$C_5$ alkyl" includes straight chain and branched chain substituents of this type, with branched chain substituents being preferred. The term "$C_3$-$C_5$ alkenyl" includes substituents of this type having either straight or branched chains and having one or two double bonds. A preferred substituent of this type is allyl. The term "$C_3$-$C_6$ alkynyl" includes substituents of this type having a straight or branched chain and at least one triple bond. A preferred member of this group is 1,1-dimethyl-2-propynyl, also called 1,1-dimethylpropargyl.

The compounds of this invention have been found to be active herbicides; that is the compounds have been found to be herbicidally active against various species of weeds. In the broadest sense, the term "weeds" refer to plants which grow in locations in which they are not desired. As will be seen from the data which follows, these compounds show various activities as pre-emergence and/or post-emergence herbicides. In some cases they have been found to show particular activity against certain weed species.

This invention, therefore, also relates to a method of controlling undesirable vegetation comprising applying to such vegetation a herbicidally effective amount of a compound as described herein, and also relates to herbicidal compositions of matter comprising a herbicidally effective amount of a compound as described herein plus an inert diluent or carrier suitable for use with herbicides.

As used herein, the term "herbicide" means a compound which controls or modifies the growth of plants, particularly of undesirable plants. By the term "herbicidally effective amount" is meant an amount of a compound which causes a controlling or modifying effect on the growth of plants. The term "plants" is meant to include germinant seeds, emerging seedlings and established vegetation including roots and above ground portions. Such modifying and controlling effects include all deviations from natural development.

In general, the compounds can be prepared by the reaction of the appropriate 2-(3-substituted phenoxy) nicotinoyl chloride with an amine:

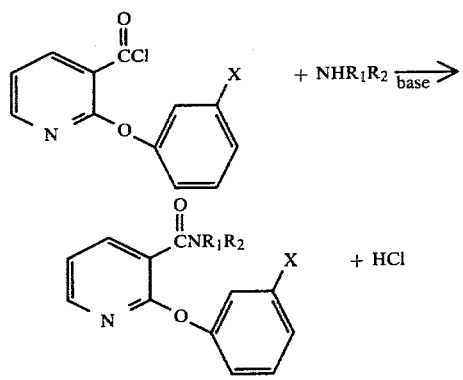

in which X, $R_1$, and $R_2$ are as previously defined. The reaction is carried out in the presence of an acid acceptor such as caustic, an additional equivalent of the reacting amine or another amine (triethylamine is preferred). Reaction temperatures may range from about 0° to about 100° C., at atmospheric pressure. Any of a number of solvents may be used, for instance, methylene chloride, diethyl ether, benzene and, preferably, toluene. The product may be recovered by first removing the by-product salt or amine salt with water, then recovering the product from the organic layer by conventional means.

The nicotinoyl chlorides are prepared from the corresponding carboxylic acids by the conventional technique of reacting the acid with a suitable chlorinating agent such as phosgene, $PCl_3$, $PCl_5$, or, preferably, thionyl chloride. Temperatures may range from about 25° to about 110° C. Solvents such as those mentioned above may be used. The acids may be prepared by reacting a meta-substituted phenol with 2-chloronicotinic acid, as described by Villani, et al., J. Medicinal Chemistry 18, 1 (1975).

The following are representative examples of the preparation of compounds according to the present invention.

EXAMPLE 1

Preparation of 2(3-trifluoromethylphenoxy)N (1,1-dimethylpropargyl)nicotinamide (Compound 3 herein)

(a) To a flask containing a solution of 45.4 grams (0.21 mole) 25% sodium methoxide in 100 milliliters of methanol were added 81.5 grams (0.5 mole) 3-trifluoromethylphenol and 15.8 grams (0.1 mole) 2-chloronicotinic acid. The reaction mass was heated and the methanol distilled off. The pot temperature was raised to 180° C. and held at that level for one hour. The mixture was then cooled to 100° C. and poured into 500 milliliters ice water. The aqueous mixture was extracted with 3 portions of 200 milliliters each, of diethyl ether, then acidified with glacial acetic acid. A solid precipitated, which was filtered, washed with water and dried, to give 25.8 grams (91.2% of theoretical yield) of 2-(3-trifluoromethylphenoxy)nicotinic acid, m.p. 149°-151° C.

(b) There are mixed 14.1 grams (0.05 mole) of the acid from step (a), 0.1 grams triethylamine hydrochloride and 150 milliliters chloroform, followed by stirring and heating to reflux. Then 6.5 grams (0.055 mole) thionyl chloride was slowly added, dropwise. After the addition was complete, the reaction mass was heated under reflux until evolution of HCl had ceased (about 30 minutes). The reaction mixture was cooled to room temperature, and the solvent was removed by vacuum distillation yielding 100 grams (66.7% of theoretical yield) of 2-(3-trifluoromethylphenoxy) nicotinoyl chloride.

(c) In a flask were mixed with stirring, 0.6 grams (0.007 mole) 1,1-dimethylpropargylamine, 0.7 grams (0.007 mole) triethylamine and 50 milliliters toluene; then a solution of 2.2 grams (0.007 mole) of the acyl chloride prepared in step (b), in 25 milliliters toluene, was added. The rate of addition was controlled so as to maintain the reaction temperature below 35° C. After the addition was complete the mixture was stirred for one hour at 45° C., then cooled and poured into 100 milliliters of toluene. The mixture was washed twice with water; the organic phase was dried, filtered and solvent removed to yield 1.6 grams (65.7% of theoretical yield) of the desired product, $n_D^{30}$ 1.5012. The structure was confirmed by mass spectrometry.

EXAMPLE 2

Preparation of 2-(3-trifluoromethylphenoxy)N,N-diallyl nicotinamide (Compound 1 herein)

In the same manner as in Example 1(a), 1.6 grams (0.016 mole) diallylamine and 2.5 grams (0.008 mole) 2-(3-trifluoromethylphenoxy)nicotinoyl chloride were mixed in 100 milliliters benzene to yield 1.6 grams (55.2% of theoretical yield) of the desired product, $n_D^{30}$ 1.5003. The structure of this compound was confirmed by mass spectrometry.

EXAMPLE 3

Preparation of 2-(3-chlorophenoxy)N-isobutylnicotinamide (Compound 7 herein)

(a) In the same manner as in Example 1(a), 15.8 grams (0.1 mole) 2-chloronicotinic acid, 64.0 grams (0.5 mole) 3-chlorophenol, 45 grams (0.21 mole) 25% sodium methoxide solution and 100 milliliters methanol were combined to produce 22.1 grams (88.6% of theoretical yield) of 2-(3-chlorophenoxy) nicotinic acid, m.p. 161°-164° C.

(b) In the same manner as in Example 1(b) the 22.1 grams of 2-(3-chlorophenoxy) nicotinic acid was combined with 13.0 grams (0.1 mole) thionyl chloride, 0.5 grams triethylamine hydrochloride and 200 milliliters chloroform to produce 23.2 grams (98.3% of theoretical yield) of 2-(3-chlorophenoxy)nicotinoyl chloride, m.p. 72°-74° C.

(c) In the same manner as in Example 1(c) 1.4 grams (0.02 mole) isobutylamine and 2.7 grams (0.01 mole) of the acyl chloride produced in step (b) were combined in 50 milliliters toluene to yield 2.8 grams (92.1% of theoretical yield) of the desired product, m.p. 86°-87° C. The structure was confirmed by mass spectrometry.

Table 1 which follows contains a list of representative compounds of the present invention.

TABLE I

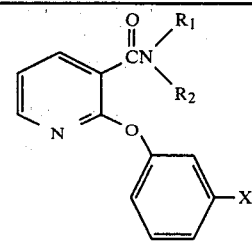

| Compound No. | X | $R_1$ | $R_2$ | m.p., °C. or $n_D^{30}$ |
|---|---|---|---|---|
| 1 | $CF_3$ | $-CH_2CH=CH_2$ | $-CH_2CH=CH_2$ | 1.5003 |
| 2 | Cl | H | $-C(CH_3)_2C\equiv CH$ | crude solid |
| 3 | $CF_3$ | H | $-C(CH_3)_2C\equiv CH$ | 1.5012 |
| 4 | $CH_3$ | H | $i\text{-}C_3H_7$ | 65-66 |
| 5 | $CH_3$ | H | $-CH_2CH=CH_2$ | 49-50 |
| 6 | Cl | H | $i\text{-}C_3H_7$ | 72-75 |
| 7 | Cl | H | $i\text{-}C_4H_9$ | 86-87 |
| 8 | Cl | $-CH_2CH=CH_2$ | $-CH_2CH=CH_2$ | semi-solid |
| 9 | Br | H | $CH_3$ | 151-155 |
| 10 | Br | H | $i\text{-}C_3H_7$ | semi-solid |
| 11 | $C_2H_5$ | H | $i\text{-}C_3H_7$ | 56-58 |
| 12 | $C_2H_5$ | H | $i\text{-}C_4H_9$ | 1.5520 |
| 13 | $C_2H_5$ | H | $-CH_2CH=CH_2$ | 44-45 |

A. Pre-emergence Herbicide Screening Test

Using an analytical balance, 20 milligrams of the compound to be tested was weighed out on a piece of glassine weighing paper. The paper and compound were placed in a 30 milliliter wide-mouth bottle and 3 milliliters of acetone containing 1% polyoxyethylene sorbitan monolaurate emulsifying agent was added to dissolve the compound. If the material was not soluble in acetone, another solvent such as water, alcohol or dimethylformamide (DMF) was used instead. When DMF was used, only 0.5 milliliters or less was used to dissolve the compound and then another solvent was used to make the volume up to 3 milliliters. The 3 milliliter solution was sprayed uniformly on the soil contained in a small flat one day after planting weed seeds in the flat of soil. A No. 152 DeVilbiss atomizer was used to apply the spray using compressed air at a pressure of 5 lb/sq. in. (0.35 kg/cm$^2$). The rate of application was 8 lb./acre (8.96 kg/hectare), and the spray volume was 143 gal./acre (1338 liter/hectare).

On the day preceding treatment, the flat was filled to a depth of 2 inches with loamy sand soil. Seeds of seven different species were planted in individual rows using one species per row across the width of the flat. The seeds were covered with soil so that they were planted at a depth of 0.5 inch (1.3 cm). The seeds used were hairy crabgrass (*Digitaria sanguinalis*), green foxtail (*Setaria viridis*) watergrass (*Echinochloa crusgalli*), red oat (*Avena sativa*), redroot pigweed (*Amaranthus retroflexus*), Indian mustard (*Brassica juncea*) and curlydock (*Rumex crispus*). Ample seeds were planted to give about 20-50 seedlings per row after emergence depending on the size of the plants.

After treatment, the flats were placed in the greenhouse at a temperature of 70-85° F. (21.1 to 29.4° C.) and watered by sprinkling. Two weeks after treatment the degree of injury or control was determined by comparison with untreated check plants of the same age. The injury rating from 0 to 100% was recorded for each species as percent control, with 0% representing no injury and 100% representing complete kill.

B. Post-emergence Herbicide Screening Test

Seeds of six plant species, including hairy crabgrass, watergrass, red oat, mustard, curly dock and pinto beans (*Phaseolus vulgaris*) were planted in flats. The flats were placed in the greenhouse at 70-85° F. (21.1 to 29.4° C.) and watered daily with a sprinkler. About 10 to 14 days after planting when the primary leaves of the bean plants were almost fully expanded and the first trifoliate leaves were just starting to form, the plants were sprayed. The spray was prepared by weighing out 20 milligrams of the test compound, dissolving it in 2.5 milliliters of acetone containing 1% polyoxyethylene sorbitan monolaurate emulsifying agent and then adding 2.5 milliliters of water. The solution was sprayed on the foliage using a No. 152 DeVilbiss atomizer at an air pressure of 5 lb./sq. in. (0.35 kg/cm$^2$). The rate was 8 lb./acre (8.96 kg/hectare). The spray volume was 238 gal./acre (2226 liters/hectare).

The results of the above evaluations are shown in the following Table II.

Compounds 1-6 were tested for pre-emergence control on six plant species and post-emergence control on seven plant species, as described above. However, crabgrass was not included in the evaluation of compounds 7-13.

TABLE II

| Compound No. | Pre-emergence Control | Post-emergence Control |
|---|---|---|
| 1 | 58 | 12 |
| 2 | 61 | 38 |
| 3 | 85 | 57 |
| 4 | 53 | 12 |
| 5 | 32 | 16 |
| 6 | 82 | 54 |
| 7 | 65 | 57 |
| 8 | 35 | 18 |
| 9 | 78 | 34 |
| 10 | 43 | 20 |
| 11 | 45 | 16 |
| 12 | 33 | 0 |
| 13 | 39 | 10 |

In practice, a pure compound can be used as a herbicide. However, in general, the compounds are first formulated with one or more inert carriers or diluents suitable for herbicidal use, before being applied.

The compositions for formulations, including a compound as described herein, may take and be used in any one of a number of solid or liquid forms. Examples of solid forms are dusts, granules, tablets, powders and the like. Examples of liquid forms are emulsions, solutions, suspensions, emulsifiable concentrates and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives; thickners; binders; anti-foaming agents; and other substances as mentioned herein. Such carriers or diluents included in such compositions or formulations may include, for example, ground natural minerals such as kaolins, alumina, calcium carbonate, silica, kieselguhr, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders and pastes are obtained by mixing and grinding an active compound with one or more dispersing agents and/or solid carriers or diluents. Also included are wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylene, or higher boiling aromatic hydrocarbons. To obtain suspensions or emulsions in water, wetting agents are also added.

It is possible to use highly concentrated liquid compositions of those compounds which are liquids, containing up to about 95% by weight of the active compound, or even the 100% active compound alone, when applying the compound in the form of a finely divided liquid by use of various atomizing equipment, for example, by airplane crop spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: wettable powders —20 to 90% active compound; oil suspensions, emulsions, solutions and emulsifiable concentrates —5 to 90% active compound; aqueous suspensions —10 to 50% active compound; dusts and powders —1 to 25% active compound; granules and pellets —1 to 20% active compound.

The rate of application of the active compound to a locus to be controlled will depend on the nature of the seeds and plants to be controlled and will vary from about 0.05 to about 50 pounds per acre (about 0.06 to about 56 kg./ha.).

In addition to the active compound and the various agents utilized in preparing compositions and formulations mentioned above, such compositions may also contain one or more other active compounds of the type mentioned herein as well as other active pesticidal agents, such as herbicides, fungicides, insecticides, acaricides, nematocides, bactericides and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus.

Compositions containing one or more of the active compounds described, in a herbicidally effective amount, may be applied to the plant or locus to be controlled in any conventional manner. Thus, powders and various liquid compositions containing the active compound can be applied by the use of powder dusters, boom and hand sprayers and spray dusters, or applied from airplanes as dusts or sprays. When applied in the latter method they may be effective in very low dosages. To modify or control growth of germinating seeds or emerging seedlings liquid compositions may be applied to the soil with conventional methods and may be distributed in the soil to a depth of one-half inch below the soil surface. The compositions need not be admixed with the soil particles but can be applied merely by sprinkling on the surface of the soil.

Compositions including active compounds may also be applied by addition to irrigation waters supplied to the field to be treated. This method of application permits penetration of the compounds into the soil as the water is absorbed therein.

Compositions applied to the surface of the soil can be distributed below the surface of the soil by conventional means such as discing or mixing operations.

What is claimed is:

1. A compound having the formula

[structure]

in which X is chloro, bromo, trifluoromethyl, methyl or ethyl; $R_1$ is hydrogen or $C_3$–$C_5$ alkenyl and $R_2$ is:
 (a) $C_3$–$C_5$ alkenyl if $R_1$ is $C_3$–$C_5$ alkenyl;
 (b) $C_3$–$C_5$ alkyl, $C_3$–$C_5$ alkenyl or $C_3$–$C_6$ alkynyl if X is chloro, methyl, ethyl, or trifluoromethyl and $R_1$ is hydrogen; and
 (c) $C_1$–$C_5$ alkyl, $C_3$–$C_5$ alkenyl or $C_3$–$C_6$ alkynyl if X is bromo and $R_1$ is hydrogen.

2. A compound according to claim 1 in which X is chloro, methyl or trifluoromethyl; $R_1$ is hydrogen and $R_2$ is $C_3$–$C_5$ alkyl.

3. A compound according to claim 1 in which X is chloro, methyl or trifluoromethyl; $R_1$ is hydrogen and $R_2$ is $C_3$–$C_5$ alkenyl.

4. A compound according to claim 1 in which X is chloro, methyl or trifluoromethyl; $R_1$ is hydrogen and $R_2$ is $C_3$–$C_6$ alkynyl.

5. A compound according to claim 1 in which X is bromo, $R_1$ is hydrogen and $R_2$ is $C_1$–$C_5$ alkyl, $C_3$–$C_5$ alkenyl, or $C_3$–$C_6$ alkynyl.

6. A compound according to claim 1 in which X is trifuloromethyl and $R_1$ and $R_2$ are each allyl.

7. A compound according to claim 1 in which X is chloro, $R_1$ is hydrogen and $R_2$ is 1,1-dimethyl-2-propynyl.

8. A compound according to claim 1 in which X is trifluoromethyl, $R_1$ is hydrogen and $R_2$ is 1,1-dimethyl-2-propynyl.

9. A compound according to claim 1 in which X is methyl, $R_1$ is hydrogen and $R_2$ is isopropyl.

10. A compound according to claim 1 in which X is methyl, $R_1$ is hydrogen and $R_2$ is allyl.

11. A compound according to claim 1 in which X is chloro, $R_1$ is hydrogen and $R_2$ is isopropyl.

12. A compound according to claim 1 in which X is chloro, $R_1$ is hydrogen and $R_2$ is isobutyl.

13. A compound according to claim 1 in which X is chloro and $R_1$ and $R_2$ are each allyl.

14. A compound according to claim 1 in which X is bromo, $R_1$ is hydrogen and $R_2$ is methyl.

15. A compound according to claim 1 in which X is bromo, $R_1$ is hydrogen and $R_2$ is isopropyl.

16. A compound according to claim 1 in which X is ethyl, $R_1$ is hydrogen and $R_2$ is isopropyl.

17. A compound according to claim 1 in which X is ethyl, $R_1$ is hydrogen and $R_2$ is isobutyl.

18. A compound according to claim 1 in which X is ethyl, $R_1$ is hydrogen and $R_2$ is allyl.

19. A method of controlling undesirable vegetation comprising applying to the vegetation or the locus thereof a herbicidally effective amount of a compound having the formula

[structure]

in which X is chloro, bromo, trifluoromethyl, methyl or ethyl; $R_1$ is hydrogen or $C_3$–$C_5$ alkenyl and $R_2$ is:
 (a) $C_3$–$C_5$ alkenyl if $R_1$ is $C_3$–$C_5$ alkenyl;
 (b) $C_3$–$C_5$ alkyl, $C_3$–$C_5$ alkenyl or $C_3$–$C_6$ alkynyl if X is chloro, methyl, ethyl or trifluoromethyl and $R_1$ is hydrogen; and
 (c) $C_1$–$C_5$ alkyl, $C_3$–$C_5$ alkenyl or $C_3$–$C_6$ alkynyl if X is bromo and $R_1$ is hydrogen.

20. A method according to claim 19 in which X is chloro, methyl or trifluoromethyl; $R_1$ is hydrogen and $R_2$ is $C_3$–$C_5$ alkyl.

21. A method according to claim 19 in which X is chloro, methyl or trifluoromethyl; $R_1$ is hydrogen and $R_2$ is $C_3$–$C_5$ alkenyl.

22. A method according to claim 19 in which X is chloro, methyl or trifluoromethyl; $R_1$ is hydrogen and $R_2$ is $C_3$–$C_6$ alkynyl.

23. A method according to claim 19 in which X is bromo, $R_1$ is hydrogen and $R_2$ is $C_1$–$C_5$ alkyl, $C_3$–$C_5$ alkenyl or $C_3$–$C_6$ alkynyl.

24. A herbicidal composition of matter comprising:
 (i) A herbicidally effective amount of a compound having the formula

[structure]

in which X is chloro, bromo, trifluoromethyl, methyl or ethyl; $R_1$ is hydrogen or $C_3$–$C_5$ alkenyl and $R_2$ is:
 (a) $C_3$–$C_5$ alkenyl if $R_1$ is $C_3$–$C_5$ alkenyl;
 (b) $C_3$–$C_5$ alkyl, $C_3$–$C_5$ alkenyl or $C_3$–$C_6$ alkynyl if X is chloro, methyl, ethyl or trifluoromethyl and $R_1$ is hydrogen; and
 (c) $C_1$–$C_5$ alkyl, $C_3$–$C_5$ alkenyl or $C_3$–$C_6$ alkynyl if X is bromo and $R_1$ is hydrogen, and
 (ii) a herbicidally suitable inert carrier or diluent.

* * * * *